US009631030B2

(12) United States Patent
Hernández Pascual et al.

(10) Patent No.: US 9,631,030 B2
(45) Date of Patent: Apr. 25, 2017

(54) ADMINISTERING ANTIBODIES OR FRAGMENTS THEREOF WHICH BIND HEMOPEXIN FOR THE TREATMENT OF OCULAR DISEASES

(71) Applicant: FUNDACIÓ HOSPITAL UNIVERSITARI VALL D'HEBRON—INSTITUT DE RECERCA, Barcelona (ES)

(72) Inventors: Cristina Hernández Pascual, Barcelona (ES); Rafael Simó Canonge, Sant Cugat del Vallès (ES)

(73) Assignee: FUNDACIÓ HOSPITAL UNIVERSITARI VALL D'HEBRON—INSTITUT DE RECERCA, Barcelona (ES)

( * ) Notice: Subject to any disclaimer, the term of this patent is extended or adjusted under 35 U.S.C. 154(b) by 83 days.

(21) Appl. No.: 14/398,110

(22) PCT Filed: Apr. 29, 2013

(86) PCT No.: PCT/EP2013/058836
§ 371 (c)(1),
(2) Date: Oct. 30, 2014

(87) PCT Pub. No.: WO2013/164290
PCT Pub. Date: Nov. 7, 2013

(65) Prior Publication Data
US 2015/0110795 A1 Apr. 23, 2015

(30) Foreign Application Priority Data

Apr. 30, 2012 (EP) .................... 12382161

(51) Int. Cl.
C07K 16/40 (2006.01)
C07K 16/18 (2006.01)
A61K 39/00 (2006.01)
(52) U.S. Cl.
CPC .............. C07K 16/40 (2013.01); C07K 16/18 (2013.01); A61K 2039/505 (2013.01); C07K 2317/70 (2013.01)
(58) Field of Classification Search
None
See application file for complete search history.

(56) References Cited

FOREIGN PATENT DOCUMENTS

| JP | 2002220349 | | 8/2002 |
| KR | 100792630 | | 1/2008 |
| KR | 100792630 | B1 | 1/2008 |
| WO | 2008087049 | A1 | 7/2008 |
| WO | 2008141285 | A2 | 11/2008 |
| WO | WO 2013049321 | A1 * | 4/2013 ......... A61K 38/1709 |

OTHER PUBLICATIONS

Moyer et al., Infect Immun. Apr. 2008;76(4):1358-67. doi: 10.1128/IAI.01330-07. Epub Feb. 11, 2008.*
Hunt et al., J Cell Physiol. Jul. 1996;168(1):71-80. (Hunt1).*
Hunt et al., J Cell Physiol. Jul. 1996;168(1):81-6. (Hunt2).*
Chen et al., Exp Eye Res. Jul. 1998;67(1):83-93.*
M. Garcia Ramirez et al., Proteomic Analysis of Human Vitreous Fluid by Fluorescence-based difference Gel Electrophoresis (DIGE): A New Strategy for Identifying Potential Candidates in the Pathogenesis of Proliferative Diabetic Retinopathy, Diabetologia (2007), Mar. 23, 2007, pp. 1294-1303, vol. 50, Springer-Verlag, New York, NY.
Ben-Bo Gao et al., Characterization of Vitreous Proteome in Diabetes without Diabetic Retinopathy and Diabetes with Proliferative Diabetic Retinopahty, Journal of Proteome Research, Received Feb. 12, 2008, published on Web Jun. 1, 2008, pp. 2516-2525, vol. 7, No. 6 American Chemical Society, New York, NY.
Cristina Hernández et al., New pathogenic candidates for diabetic macular edema detected by proteomic analysis, Diabetes Care, Jul. 1, 2010, pp. e92, vol. 33, No. 7, care.diabetesjournals.org, American Diabetes Association, Alexandria, VA.
Marta García-Ramírez et al., Measuring Permeability in Human Retinal Epithelial Cells (ARPE-19). Implications for the Study of Diabetic Retinopathy, Methods in Molecular Biology 763, Permeability Barrier Methods and Protocols, 2011, pp. 179-194, vol. 763, Springer Science+Business Media, New York, NY.
Jose Cunha-Vaz, The Blood-Retinal Barrier in Retinal Disease, Posterior Segment Retina, European Ophthalmic Review, 2009, received Jul. 29, 2009, Accepted Oct. 27, 2009, pp. 105-108, vol. 3, Touch Digital Media Ltd., Goring on Thames, UK.
Jose Cunha-Vaz et al., Blood-retinal barrier, European Journal Ophthalmology, 2011, accepted Oct. 26, 2010, pp. 3-9, vol. No. 21 (Suppl. 6), Wichtig Editore, Milano, Italy.
L. Tong et al., Association of macular involvement with proliferative retinopathy in Type 2 diabetes, Diabetic Medicine, accepted Dec. 3, 2000, pp. 388-394, vol. No. 18, Diabetes UK. Diabetic Medicine, Wiley Online Library, Hoboken, NJ with operations in US, Europe, Asia, Canada and Australia.
Cristina Hernández et al., Overexpression of hemopexin in the diabetic eye:a new pathogenic candidate for diabetic macular edema, Diabetes Care, Sep. 1, 2013, pp. 2815-2821, vol. No. 36, No. 9, care.diabetesjournals.org, American Diabetes Association, Alexandria, VA.

(Continued)

Primary Examiner — Michael Szperka
(74) Attorney, Agent, or Firm — Peter B. Scull; Hamilton, DeSanctis & Cha LLP

(57) ABSTRACT

Administering antibodies or fragments thereof which bind hemopexin for use in the treatment of retinal diseases, in particular a retinal disease in which there is a dysfunction of the external blood-retinal barrier, the dysfunction being an impairment of the blood-retinal barrier. Pharmaceutical and veterinary compositions are also disclosed in which the antibodies or fragments thereof are present. The compositions may be applied in wide spectra of ocular diseases.

19 Claims, 2 Drawing Sheets

(56) References Cited

OTHER PUBLICATIONS

Marcia R. Mauk et al., An alternative view of the proposed alternative activities of hemopexin, Protein Science, published May 1, 2011, pp. 791-805, vol. No. 20, No. 5, proteinscience.org, Wiley-Blackwell, Hoboken, NJ with operations in US, Europe, Asia, Canada, and Australia.

Richard C. Hunt et al., Hemopexin in the human retina: Protection of the retina against heme-mediated toxicity, Journal of Cellular Physiology, 1996, Jul. 1, 1996, pp. 71-80, vol. 168 No. 1, Wiley-Liss, Inc., Wiley Online Library, Hoboken, NJ with operations in US, Europe, Asia, Canada and Australia.

Richard C. Hunt et al., Heme-mediated reactive oxygen species toxicity to retinal pigment epithelial cells is reduced by hemopexin, Journal of Cellular Physiology, Jul. 1, 1996, pp. 81-86, vol. 168, No. 1, Wiley-Liss, Inc., Wiley Online Library, Hoboken, NJ with operations in US, Europe, Asia, Canada and Australia.

International Search Report and Written Opinion of the International Searching Authority, Search Report, Application No. PCT/EP2013/058836 issued by the European Patent Office, Rijswijk, Netherlands, dated Dec. 20, 2013.

* cited by examiner

ADMINISTERING ANTIBODIES OR FRAGMENTS THEREOF WHICH BIND HEMOPEXIN FOR THE TREATMENT OF OCULAR DISEASES

The present disclosure relates to the field of medical approaches for ocular diseases that may lead to partial or total blindness. Provided are useful tools to be applied in medicine, including antibodies or fragments thereof.

BACKGROUND

Several are the diseases that affect the retina (retinal diseases) including age related macular degeneration, retinitis pigmentosa, diabetic retinopathy, macular edema and other inherited retinal degenerations, uveitis, retinal detachment, and eye cancers. The retina is the light sensitive portion of the eye, and is a complex tissue containing specialized photoreceptor cells, the cones and the rods. The photoreceptors connect to a network of nerve cells for the local processing of visual information, which is sent to the brain for obtaining a visual image. The rods are mostly located away from the centre of the eye in the retinal periphery. The highest concentration of cones is found at the center of the retina, the macula, which is necessary for visual acuity.

Under the retina is located the choroid. The retinal pigment epithelium (RPE) is a monolayer of pigmented cells situated between the neuroretina and the choroids. The RPE is the pigmented cell layer just outside the neurosensory retina that nourishes retinal visual cells. RPE cells protect, support, and feed the light sensitive retina. The dysfunction, disruption and/or loss of these RPE cells play a critical role in the development of the vision loss. Thus, RPE cells are often the first cells to degenerate or suffer damage as a result of a traumatizing event or condition.

Another structure of the eye being of great importance in many of the retinal diseases is the blood-retinal barrier (BRB), also called hemato-retinal barrier. The BRB is constituted by the inner blood-retinal barrier and the external blood-retinal barrier. Inner blood-retinal barrier is formed by the tight junctions of endothelial cells. External blood-retinal barrier is constituted by the RPE, which cells are also connected by tight junctions. Tight junctions between RPE cells are essential to control the transport of liquid and soluble compounds through the BRB, as well as to avoid any toxics into the retina. Therefore, RPE is a key component of the external blood-retinal barrier to assure retina integrity. The two most frequent retinal diseases that are due to an impairment of the external BRB thus resulting in retinal edema are diabetic macular edema and age-related macular degeneration. In addition, alteration of the BRB occurs also in a wide variety of ocular situations, such as uveitis, trauma, intraocular surgery, vascular retinopathies, hereditary dystrophies, etc. (Cunha-Vaz et al., "The Blood-Retinal Barrier in Retinal Disease", *European Ophthalmic Review*—2009, Vol. No. 3, pp.: 105-108).

Several approaches to identify the causes of many of the retinal diseases have been performed. One of them is based on the performance of proteomic analysis of vitreous humour. The vitreous humour is the clear gel that fills the space between the lens and the retina of the eyeball of humans and other vertebrates. It is often referred to as the vitreous body or simply "the vitreous".

The proteomic analysis by differential gel electrophoresis of the vitreous has been applied for the characterization of the proteome in Proliferative Diabetic Retinopathy and in other ocular pathologies such as Diabetic Macular Edema. Examples of this are found in Ramirez et al., "Proteomic Analysis of Human Vitreous Fluid by DIGE: a New Strategy for Identifying Potential Candidates in the Pathogenesis of Proliferative Diabetic Retinopathy", *Diabetologia* 2007, Vol. 50, pp.: 1294-1303; in Gao et al., "Characterization of Vitreous Proteome in Diabetes without Diabetic Retinopathy and Diabetes with Proliferative Diabetic Retinopahty", *Journal of Proteome Research*—2008, vol. 7, pp. 2516-2525; and in Hernández et al. "New pathogenic candidates for diabetic macular edema detected by proteomic analysis", *Diabetes Care* 2010; 33:e92.

Nowadays most of the treatments of the diseases affecting the retina are implemented in advanced stages of the diseases rather than to arrest or prevent their development. Thus, in the particular case of macular edema or in some retinopathies (proliferative or non-proliferative diabetic retinopathy) the treatment is usually based on laser photocoagulation, vitrectomy and corticosteroids intravitreal injections. All these treatments are encouraged in late-stages of these diseases, that is, there are no effective early treatments. Moreover, they imply many side effects (pain, inflammation, hemorrhage, etc.) and a high ratio of failures is in addition observed.

It is worth mentioning that all these diseases are of great impact, not only because they lead to blindness or to altered vision impeding people to develop normal life (working, walking, driving, etc.), but also because they are generally linked with highly prevalent disorders, such as diabetes mellitus (in particular the type 2), and age-related macular degeneration (AMD). The relation with high prevalent disorders makes in turn all these retinal disorders of common presence in the society, thus representing a challenge for the health institutions.

Other therapeutic approaches are based on the injection of compounds able to block the vascular endothelial growth factor (VEGF), such as the antibody Ranibizumab (trade name Lucentis), which has been approved to treat the "wet" (also known as exudative or neovascular) type of age-related macular degeneration (AMD), a common form of age-related vision loss. The antibody is intravitreally injected once a month. The most common side effects associated to this treatment in clinical trials were conjunctive hemorrhage, eye pain, vitreous floaters, increased intraocular pressure, and intraocular inflammation.

Thus, there is a need of additional therapeutically approaches to face all the diseases in which retina is affected, in particular those diseases wherein RPE and BRB are compromised.

SUMMARY

Facing with the problem of finding further therapeutic approaches to treat diseases that affect the retina, or retinal diseases, provided are new methods based on the inhibition of a key compound involved in these pathologies, the hemopexin.

Thus, a first aspect relates to an antibody or a fragment thereof that specifically binds to hemopexin for use in the treatment and/or prevention of a retinal disease in which there is a dysfunction of the external blood retinal barrier, being the dysfunction an alteration or impairment of the blood-retinal barrier for any etiology. Thus, the antibody or fragment thereof is for the use in the treatment and/or prevention of a retinal disease cursing with dysfunction of the external blood-retinal barrier, the dysfunction being an alteration or impairment of the blood-retinal barrier for any etiology.

The first aspect can alternatively be formulated as a method for treating and/or preventing retinal diseases in which there is a dysfunction (or which is the same, curses with a dysfunction) of the external blood retinal barrier, the dysfunction being an alteration or impairment of the blood-retinal barrier for any etiology, the method comprising administering an antibody or a fragment thereof that specifically binds to hemopexin to the subject in need thereof. This aspect can alternatively be formulated as the use of an antibody or a fragment thereof that specifically binds to hemopexin for the manufacture of a medicament for the treatment and/or prevention of a retinal disease in which there is a dysfunction (or curses with a dysfunction) of the external blood retinal barrier, being the dysfunction an alteration or impairment of the blood-retinal barrier for any etiology.

Hemopexin (HPX), also known as beta-1β-glycoprotein is a protein that in humans is encoded by the HPX gene and belongs to hemopexin family of proteins. Human HPX gene is located at chromosome 11 and corresponds to the GenBank entry 3263. The human translated protein has 462 amino acids and corresponds to SEQ ID NO: 1, also identified as P02790, Version 2 of Oct. 1, 1996 from UniPrit/SwissProt.

Hemopexin binds heme group with the highest affinity of any known protein. Its physiological function is scavenging the heme group released or lost by the turnover of heme proteins such as hemoglobin, and thus it protects the body from the oxidative damage that free heme can cause. In addition, hemopexin releases its bound ligand for internalization upon interacting with a specific receptor situated on the surface of liver cells. This function of hemopexin is to preserve the body's iron. Hemopexin is basically synthesized in the liver, but there exist evidences of synthesis in the brain and the retina.

In the state of the art, hemopexin has been used as biomarker for acute heart failure as indicated in WO 2008087049, as biomarker for diabetic nephropathy, according to KR 100792630 and WO 2008141285, and as biomarker of therapy test in leukemia according to JP 2002220349.

Surprisingly, and as will be illustrated in the examples below, hemopexin is able to disrupt the RPE. Based on this fact, there are herewith provided antibodies or fragments thereof which can specifically bind to several hemopexin epitopes, and can block the interaction of hemopexin with its receptor sited in the retina. All of these antibodies prevent the disruption of the RPE, or allow the restitution of the disrupted RPE which is forming part of the outer (or external) BRB.

DETAILED DESCRIPTION

Figure 1:
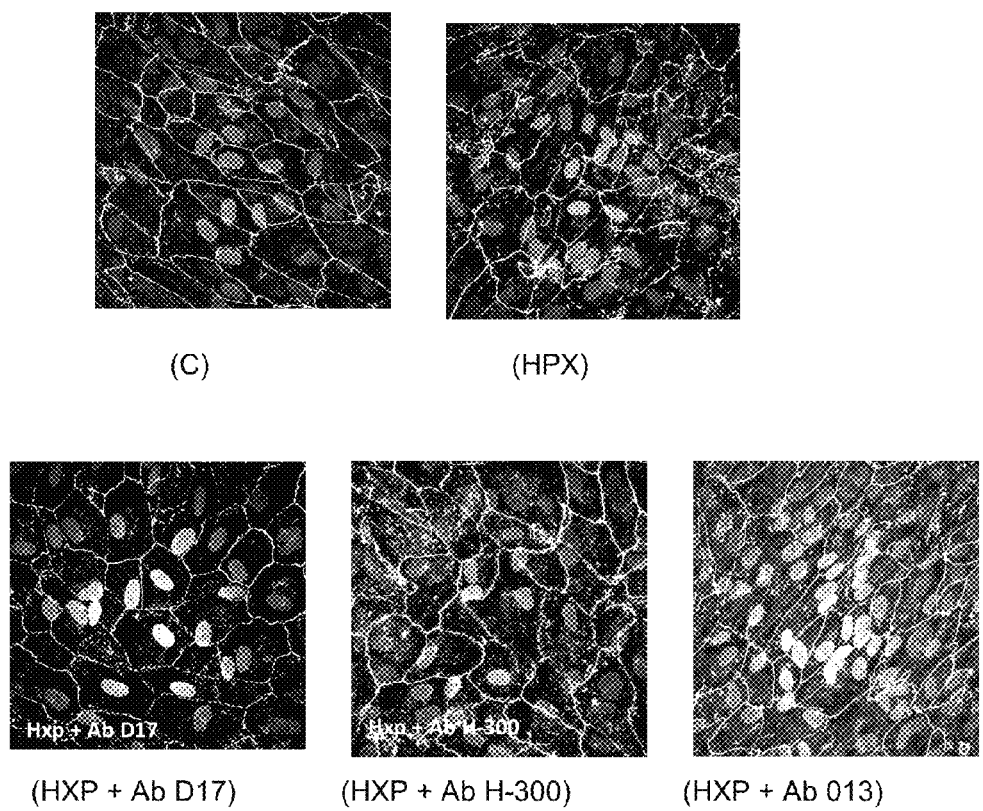
FIG. 1 is an immunofluorescence image showing tight junction protein ZO-1 (grey lines between cells) taken by confocal microscopy of a monolayer of ARPE-19 cells. Nuclei (DAPI tinction; shown as mostly spherical aggregates) are appreciated as light grey agglomerates (originally blue when visualized in the microscopy). C means control; HPX means cell monolayer after hemopexin treatment; HPX+Ab D17 means treatment with hemopexin and further goat anti-human hemopexin antibody; HX+Ab H-300 means treatment with hemopexin and further rabbit anti-human hemopexin antibody; and HX+Ab 013 means treatment with hemopexin and further mouse anti-human hemopexin antibody.

Following definitions are included in order to facilitate comprehension of the description.

In the context hereof, "epitope" is understood to mean the part of a peptide type macromolecule (or of an antigen), whose sequence and/or spatial configuration is recognized by the immune system (antibodies, T cells, B cells)

A "fragment of an antibody" refers to a part of the antibody which is of enough size and appropriate structure to bind to an epitope present in the hemopexin. Examples of fragments include F(ab), F(ab') and Fv.

The term "retinal disease" means any disease in which the retina is affected due to multiple and variant etiologies.

A retinal disease "cursing with dysfunction of the external blood-retinal barrier" or "in which there is a dysfunction of the external blood-retinal barrier", includes all retinal diseases in which the external blood-retinal barrier is altered or impaired for any etiology (Cunha-Vaz et al. "Blood-retinal barrier", Eur J Ophthalmol—2011, Vol. No. 21(S6), pp.: 3-9). These retinal diseases may be due to an impairment of the of the external blood-retinal barrier thus resulting in retinal edema. Indeed, the dysfunction (alteration or impairment) of the external blood-retinal barrier leads to an increase of the permeability of this barrier. In a preferred embodiment, the retinal disease cursing with dysfunction of the external blood-retinal barrier, or which is the same, the retinal disease due to an impairment of the external blood-retinal barrier thus resulting in retinal edema, is selected from the group consisting of age-related macular degeneration, macular edema, retinitis pigmentosa, and diabetic retinopathy. All these diseases share as common feature, that the external blood-retinal barrier, namely the layer constituted by the RPE, is disrupted for several causes. This pathological condition leads to abnormalities in the vision, which is perceived as dark-spotted, not clear, impaired or there is no vision.

Thus, in a particular embodiment, the antibody or a fragment thereof that specifically binds to hemopexin according hereto is for use in the treatment and/or prevention of a retinal disease selected from the group consisting of age-related macular degeneration, macular edema, retinitis pigmentosa, and diabetic retinopathy.

Therefore, the developments hereof relate to an antibody or a fragment thereof that specifically binds to hemopexin for use in the treatment and/or prevention of retinal diseases.

Macular edema occurs when fluid and protein deposits collect on or under the macula of the eye (a yellow central area of the retina) and causes it to thicken and swell. This is generally due to the disruption of the BRB. The swelling may distort a person's central vision, as the macula is near the center of the retina at the back of the eyeball. This area holds tightly packed cones that provide sharp, clear central vision to enable a person to see detail, form, and color that is directly in the direction of gaze. Macular edema is classified in cystoid macular edema (CME) or diffuse macular edema.

Diabetic retinopathy (DR) remains the leading cause of blindness among working-age individuals in developed countries. Whereas proliferative diabetic retinopathy (PDR) is the commonest sight-threatening lesion in type 1 diabetes, diabetic macular edema (DME) is the primary cause of poor visual acuity in type 2 diabetes. Because of the high prevalence of type 2 diabetes, DME is the main cause of visual impairment in diabetic patients. In a large population-based study, the incidence of DME over a period of 10 years was 20% in patients with type 1 diabetes whereas this rate was almost 40% in patients with type 2 diabetes (Tong et al., "Association of macular involvement with proliferative retinopathy in Type 2 diabetes", *Diabet Med*—2001, Vol. No. 18, pp.: 388-94). In addition, DME is almost invariably present when PDR is detected in type 2 diabetic patients. Neovascularization due to severe hypoxia is the hallmark of PDR whereas vascular leakage due to the breakdown of the BRB is the main event involved in the pathogenesis of DME.

Age-related macular degeneration (AMD) is a medical condition which usually affects older adults and results in a loss of vision in the center of the visual field (the macula) because of damage to the retina. Macular degeneration can make it difficult or impossible to read or recognize faces, although enough peripheral vision remains to allow other activities of daily life. The leading cause of visual loss among elderly persons is macular degeneration, signs of which use to appear after the age of 50. As documented in the western world it is a leading cause of permanent visual loss with a prevalence of 8.5% in persons under 54 years of age and of 37% in persons over 75 years of age. AMD occurs with degeneration of the macula, which is the part of the retina responsible for the sharp, central vision needed to read or to drive. It is diagnosed as either dry (non-neovascular) or wet (neovascular). Neovascular refers to growth of new blood vessels in the macula, where they are not supposed to be. The dry form is more common than the wet one, with about 85-90 percent of the patients diagnosed. The wet form of the disease usually leads to more serious vision loss.

Retinitis pigmentosa (RP) designates a group of inherited diseases that affect the retina and are characterized by a gradual destruction of the rods and cones, resulting in a progressive loss of vision and, possibly, blindness. Usually, the rod cells are the first to degenerate, causing night blindness and 'tunnel vision. Loss of central vision late in the course of the disease may occur in some cases. The rate of progression varies. To date, there is no known way to halt the degeneration of the retina or to cure the disease.

The antibody or fragment thereof, referred to in the aspects hereof, are useful in the treatment of all these diseases because they can impede or minimize the alteration of the retinal pigment epithelium forming part of the external blood-retinal barrier.

In a preferred embodiment, the antibody or fragment thereof, referred to in the aspects hereof, specifically binds to mammal hemopexin, more preferably to human hemopexin. In a preferred embodiment, the antibody or fragment thereof binds to human hemopexin of SEQ ID NO: 1. In a preferred embodiment, the antibody or fragment thereof, specifically binds to SEQ ID NO: 2, which is an epitope of human hemopexin defined by amino acids 50 to 100 of SEQ ID NO: 1. In another preferred embodiment, the antibody or fragment thereof, referred in the first and second aspects, specifically binds to SEQ ID NO: 3, which is an epitope of human hemopexin defined by amino acids 163 to 462 of SEQ ID NO: 1.

In yet another preferred embodiment, the antibody or fragment thereof is a polyclonal antibody.

Also in another preferred embodiment, the antibody or fragment thereof is a monoclonal antibody.

The antibody or a fragment thereof, which specifically binds to hemopexin, for use as defined above, may be a part or an ingredient of a pharmaceutical and/or veterinary composition.

In a preferred embodiment, the antibody or a fragment thereof, which specifically binds to hemopexin, for use as defined above, is part or an ingredient of a topical pharmaceutical and/or veterinary composition. Most preferably, the antibody or a fragment thereof is part or an ingredient of a topical composition for ocular administration, such as a liquid preparation (eye drops), or an ointment.

Alternatively, the antibody or a fragment thereof, which specifically binds to hemopexin, for use as defined above, may be part or an ingredient of an injectable solution or suspension, preferably an intravitreal injectable liquid (suspension or solution). Also alternatively, the antibody or fragment thereof may be part of an orally administrable pharmaceutical and/or veterinary composition in form of tablets, pills, capsules, microcapsules, granules, suspensions, syrups, freeze-dried powders, liquid preparations, etc. Selection of the excipients and the most appropriate methods for formulation in view of the particular purpose of the composition (topical, injectable or oral administration) is within the scope of ordinary persons skilled in the art of pharmaceutical technology.

For example, when eye drops have to be formulated, they must be isotonic with drops and the solutions, suspensions or ointments include concentrations of salts from 0.7% to 0.9% w/w, for example of sodium chloride or disodium phosphate as buffering agents, preservatives, such as polyvinyl alcohol, and viscosity agents to assure permanence in the eye. Examples of viscosity agents include, among others methylcellulose derivatives (i.e. methylcellulose). On the other hand, when the antibodies or fragments thereof form part of injectable compositions, for example for intravitreal injections, they include water for injectables, Tween 20, trehalose trihydrate and buffering agents, such as disodium phosphate or salts of aminoacids (for example histidine salts).

Another aspect includes a pharmaceutical and/or veterinary composition that comprises more than one antibody or a fragment thereof that specifically binds to hemopexin. The pharmaceutical and/or veterinary composition preferably comprises more than one antibody or fragment thereof that specifically binds to hemopexin, said antibodies or fragments thereof specifically binding different epitopes of hemopexin, or the same epitope with different sensibilities and specificities. This can also be formulated as a pharmaceutical and/or veterinary composition comprising an effective amount of an antibody or a fragment thereof that specifically binds to hemopexin for use in the treatment and/or prevention of a retinal disease, in particular a retinal disease cursing with dysfunction of the external blood-retinal barrier, together with any pharmaceutically acceptable excipient and/or carrier.

In a preferred embodiment, the developments provide a pharmaceutical and/or veterinary composition that contains at least an effective amount of an antibody or a fragment thereof that specifically binds to human hemopexin of SEQ ID NO: 1, for use in the treatment and/or prevention of a retinal disease, in particular, a retinal disease cursing with dysfunction of the external blood-retinal barrier, together with adequate amounts of pharmaceutically or veterinary acceptable excipients.

In a most preferred embodiment, the pharmaceutical and/or veterinary composition comprises an antibody or fragment thereof that specifically binds to SEQ ID NO: 2, and/or an antibody or fragment thereof that specifically binds to SEQ ID NO: 3, and/or any other antibody or a fragment thereof that specifically binds to any epitope of human hemopexin of SEQ ID NO: 1.

SEQ ID NO: 2 corresponds to the of human hemopexin defined by amino acids 50 to 100 of SEQ ID NO: 1.

SEQ ID NO: 3 corresponds to the epitope of human hemopexin defined by amino acids 163 to 462 of SEQ ID NO: 1.

Also preferred is a pharmaceutical and/or veterinary composition consisting in an antibody or fragment thereof that specifically binds to SEQ ID NO: 2, and adequate amounts of pharmaceutically or veterinary acceptable excipients. Another preferred pharmaceutical and/or veterinary composition consists in an antibody or fragment thereof that specifically binds to SEQ ID NO: 3, and adequate amounts of pharmaceutically or veterinary acceptable excipients.

Also another preferred embodiment is a pharmaceutical and/or veterinary composition that consists in an antibody or fragment thereof that specifically binds to SEQ ID NO: 2, an antibody or fragment thereof that specifically binds to SEQ ID NO: 3, and adequate amounts of pharmaceutically or veterinary acceptable excipients. Another preferred embodiment is a pharmaceutical and/or veterinary composition that consists in an antibody or fragment thereof that specifically binds to SEQ ID NO: 2, an antibody or fragment thereof that specifically binds to SEQ ID NO: 3, an antibody or a fragment thereof that specifically binds to a sequence of human hemopexin of SEQ ID NO: 1, said sequence being different from SEQ ID NO: 2 and SEQ ID NO: 3, and adequate amounts of pharmaceutically or veterinary acceptable excipients.

In this regard, the pharmaceutical and/or veterinary composition for the use according hereto may be prepared to be administered by several means, especially including topical administration, most preferably ocular topical administration in the form of liquid preparations (solutions, suspensions) to be applied as eye drops, or in the form of ointments or creams also applicable to the eyes.

Thus, in a preferred embodiment, the pharmaceutical and veterinary compositions are topical compositions. In a more preferred embodiment, the topical composition is a topical composition for ocular administration, such as a liquid preparation (eye drops), or an ointment.

Although topical administration is preferred, other forms are possible, such as injectable or oral administration. Therefore, the composition containing the effective amount of the antibody/ies or fragment/s thereof can be administered as an injectable solution or suspension, preferably an intravitreal injectable liquid (suspension or solution). Also alternatively, the composition can be administered orally in form of tablets, pills, capsules, microcapsules, granules, suspensions, syrups, freeze-dried powders, liquid preparations, etc. Selection of the excipients and the most appropriate methods for formulation in view of the particular purpose of the composition (topical, injectable or oral administration) is within the scope of ordinary persons skilled in the art of pharmaceutical technology.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. Suitable carriers, excipients, etc. can be found in standard pharmaceutical texts, and include, as a way of example preservatives, agglutinants, humectants, emollients, and antioxidants. Likewise, the term "veterinary acceptable" means suitable for use in contact with the tissues of a non-human animal.

The term "effective amount" as used herein, means an amount of an active agent (antibody or fragment thereof) high enough to deliver the desired benefit (either the treatment or prevention of the illness), but low enough to avoid serious side effects within the scope of medical judgment.

Throughout the description and claims the word "comprise" and variations of the word, are not intended to exclude other technical features, additives, components, or steps. Furthermore, the word "comprise" and its variations encompasses the term "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

Example 1

Hemopexin Disrupts External Blood-Retinal Barrier

In order to illustrate the effect of the antibodies or fragments thereof for use in the treatment and/or prevention of a retinal disease due to an impairment of (or cursing with dysfunction of) the external blood-retinal barrier, namely with alteration of RPE, developed and described herein is a permeability assay with the cell line ARPE-19 (ATCC, Manassas, Va.), which is an spontaneous immortalized cell line of RPE. Cultures were maintained at 37° C. and $CO_2$ (5%) in bottles of 75 $cm^2$ and standard media (DMEN Ham's F-12) supplemented with fetal bovine serum at 10% (SBF, Hyclone, Cultek, Barcelona, Spain). Streptomycin (100 mg/ml) and penicillin (100 U/ml) were added as preservatives. Glucose concentration was adjusted at 25 mM. The media was replaced every 3 days. ARPE-19 cells from passage 20 were used for permeability studies.

The permeability of the external BRB which is the one including the RPE was analyzed following the methodology disclosed by García-Ramírez M et al., "Measuring Permeability in Human Retinal Epithelial Cells (ARPE-19): implications for the Study of Diabetic Retinopathy", *Methods Mol Biol*—2011; Vol. No. 763, pp.: 179-94

Briefly, ARPE-19 cells were seeded at a density of 400.000 cells/ml that represented 80.000 RPE cells/well in polystyrene inserts having a surface of 0.33 $cm^2$ (HTS-Transwells; Costar; Corning Inc, NY, USA). At this density the cells formed a monolayer, which was cultivated for 15 days, replacing the media every 3 days. At day 15 different treatments (4 replicates/treatment) were applied via the apical part of the wells:

Treatment with Hemopexin

Apical media of the insert in the apical part was replaced by deprived serum media (Bovine fetal serum, BFS at 1%), and plasmatic hemopexin was added (50 µg/mL, SIGMA, Madrid, España). 15 hours later, fluorescent dextrane was added (10 kDa; SIGMA, Madrid, España) at 100 μg/mL. Afterwards 200 μL of media in the basal part of the insert were removed at intervals of 30 min, and replaced by fresh media. Absorbancies were read at an exciting wavelength of 485 nm, and an emission wavelength of 528 nm in the spectrophotometer SpectraMax Gemini (Molecular Devices, Sunnyvale, Calif.). Dextran concentration was determined by fluorescence extrapolation in a standard curve.

Treatment with Antibodies Anti-Human Hemopexin of SEQ ID NO: 1.

For the treatment with antibodies, media with hemopexin (50 μg/mL) was prepared in the tubs and the extract concentration of antibody required (0.75 μg/mL) was added to the solution. Then, the solutions were vortexed briefly and incubated 1 h. at 37° C.

The antibodies were: goat anti-human hemopexin antibody Ab D17 (treatment HPX+Ab D17) (Santa Cruz Biotechnology, Inc, Santa Cruz, Calif., USA); rabbit anti-human hemopexin antibody Ab H-300 (treatment HPX+Ab H-300) (Santa Cruz Biotechnology, Inc, Santa Cruz, Calif., USA); and mouse anti-human hemopexin Ab 013 (treatment HPX+Ab 013) (Santa Cruz Biotechnology, Inc, Santa Cruz, Calif., USA).

Goat anti-human hemopexin antibody Ab D17 is a polyclonal antibody that specifically binds to SEQ ID NO: 2, which is the epitope of human hemopexin defined by amino acids 50 to 100 of SEQ ID NO: 1.

Rabbit anti-human hemopexin antibody Ab H-300 is a polyclonal antibody that specifically binds to SEQ ID NO: 3, which is the epitope of human hemopexin defined by amino acids 163 to 462 of SEQ ID NO: 1.

Mouse anti-human hemopexin Ab 013 is a monoclonal antibody raised against full length native hemopexin of human origin.

Figure 2:
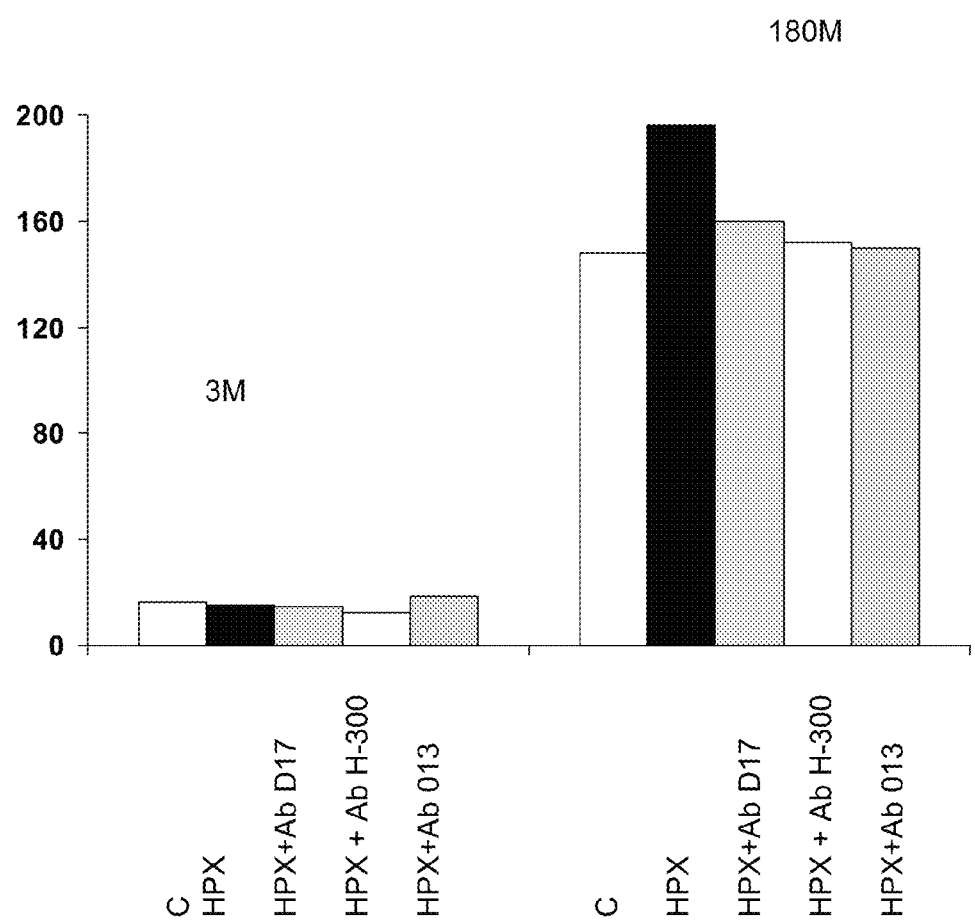
FIG. 2 is a bar diagram showing the dextrane permeability of ARPE-19 cells with different external conditions. Abbreviations mean the same as in FIG. 1. 3M and 180M mean 3 minutes and 180 minutes, respectively.

FIG. 2 shows the dextrane permeability of ARPE-19 cells, measured as the detectable fluorescent dextrane in the 200 μL of media removed from the basal part of the inserts (at 3 minutes from addition of the treatment or at 180 minutes), of the treatment with hemopexin (HPX) and antibodies. The treatment with hemopexin produces a meaningful permeability increase, as deduced from the high bar HPX, said increase being prevented if hemopexin was neutralized with the different antibodies.

On the other hand, an immunohistochemical analysis of the ARPE-19 monolayer was done. Cells that were submitted to the action of HPX, or HPX and one of the antibodies mentioned above.

For the treatment with antibodies a solution of 50 μg/mL of hemopexin was prepared in Eppendorf in deprived media (DMEN Ham's F-12 SBF 1%). Further, a solution with the antibody was also added. The solution was vortexed and incubated for 1 h at 37° C.

For this assay ARPE-19 cell monolayers grown on crystal for 15 days (Thermo scientific, Menzel-Glaser; Braunschweig, GE), were treated with hemopexin and the antibodies and then were fixed with cool methanol (−20° C.) for 10 minutes, washed with phosphate buffer saline (PBS), and blocked and permeabilized overnight (at 4° C.) with bovine serum albumine (at 2%) in PBS and Tween 0.05%. Further, they were incubated with primary antibody mouse anti-human ZO-1 (zona occludens-1; 1:200, Zymed Laboratories Inc., San Francisco, Calif.,) 1 h. As secondary antibody Alexa 594 anti-mouse (1:200, Invitrogen, San Diego, Calif.) was used for 1 h.

Preparations were mounted with a fluorescence mounting medium containing 4',6-diamidino-2-phenylindole (DAPI) to stain nuclei (Vector Laboratories; Burlingame, Calif.), and then were visualized in a spectral confocal microscope FV1000 (Olympus, Hamburg, Germany). Originally images were captured in the immersion microscope objective lense (at 60×).

The result of this assay can be seen in FIG. 1. The control (C, no treatment) shows organized cells, meanwhile in the treatment with hemopexin (HPX) a disorganized monolayer can be seen. Prevention of disorganization is achieved with antibodies anti-human hemopexin.

All these data taken together allow concluding that, surprisingly, the antibodies raised against hemopexin avoid the disruption of a model of retinal pigment epithelium, thus being able to treat retinal diseases, particularly retinal diseases cursing with alteration of retinal pigment epithelium, and more generally cursing with dysfunction of the external blood-retinal barrier, being the dysfunction an alteration or impairment of the blood-retinal barrier for any etiology or cause.

Besides, and with the aim of investigating more in-depth the mechanisms of action involved in this process, provided herewith is evidence of the role of hemopexin as an agent able to disrupt the RPE, thus causing the disorganization if intercellular unions (tight junctions). This disorganization of one of the main components of the external blood-retinal barrier functionally affecting the entire barrier, for example, causing an increased permeability. Increasing the permeability of the barrier leads to serious problems derived from altered control of the transport of liquid and soluble compounds through the blood-retinal barrier, such as nutrients. In addition the impairment of the barrier makes the retina accessible to toxic compounds.

The embodiments proposed herein alone or taken in combination with each other, as well as with the examples above disclosed, allow concluding that antibodies or fragments thereof which can specifically bind to several hemopexin epitopes, are able to efficiently block the interaction of hemopexin with its receptor sited in the retina, thus preventing the disruption of the RPE, or allowing the restitution of the disrupted RPE. This represents even an interesting and also efficient approach for treating and/or preventing a retinal disease, in particular those cursing with dysfunction of the external blood-retinal barrier, among which there are included diseases evolving high functional limitations due to the effect of compromising vision.

The invention claimed is:

1. A method for the treatment of a retinal disease in which there is a dysfunction of the external blood retinal barrier, the dysfunction being a non-hemorrhagic impairment of the blood retinal barrier, the method comprising:
    administering a therapeutically effective amount of an antibody or a fragment thereof that specifically binds to hemopexin, together with pharmaceutical excipients or carriers, in a patient.

2. The method of claim 1, wherein the antibody or a fragment thereof specifically binds mammal hemopexin.

3. The method of claim 1, wherein the antibody or a fragment thereof specifically binds human hemopexin of SEQ ID NO: 1.

4. The method of claim 1, wherein the antibody or a fragment thereof specifically binds to SEQ ID NO: 2.

5. The method of claim 1, wherein the antibody or a fragment thereof specifically binds to SEQ ID NO: 3.

6. The method of claim 1, wherein the antibody is a polyclonal antibody or a fragment from said polyclonal antibody.

7. The method of claim 1, wherein the antibody is a monoclonal antibody or a fragment from said monoclonal antibody.

8. The method of claim 1, including treating a retinal disease selected from the group consisting of age-related macular degeneration, macular edema, retinitis pigmentosa, and diabetic retinopathy.

9. The method of claim 1, wherein the antibody or a fragment thereof is an ingredient of a pharmaceutical and/or veterinary composition.

10. The method of claim 1, wherein the antibody or a fragment thereof is an ingredient of a topical pharmaceutical and/or veterinary composition.

11. The method of claim 10, wherein the administering of the antibody or a fragment thereof is ocular administering.

12. The method of claim 1, wherein the antibody or a fragment thereof is an ingredient of an injectable pharmaceutical and/or veterinary composition.

13. The method of claim 12, wherein the administering of the antibody or a fragment thereof intravitreal administering.

14. The method of claim 2, wherein the antibody is a polyclonal antibody or a fragment from said polyclonal antibody.

15. The method of claim 3, wherein the antibody is a polyclonal antibody or a fragment from said polyclonal antibody.

16. The method of claim 4, wherein the antibody is a polyclonal antibody or a fragment from said polyclonal antibody.

17. The method of claim 5, wherein the antibody is a polyclonal antibody or a fragment from said polyclonal antibody.

18. The method of claim 3, wherein the antibody is a monoclonal antibody or a fragment from said monoclonal antibody.

19. The method of claim 1 wherein the patient is a human.

* * * * *

SEQUENCE LISTING

```
<160> NUMBER OF SEQ ID NOS: 3

<210> SEQ ID NO 1
<211> LENGTH: 462
<212> TYPE: PRT
<213> ORGANISM: Homo sapiens
```

<400> SEQUENCE: 1

```
Met Ala Arg Val Leu Gly Ala Pro Val Ala Leu Gly Leu Trp Ser Leu
1               5                   10                  15

Cys Trp Ser Leu Ala Ile Ala Thr Pro Leu Pro Pro Thr Ser Ala His
            20                  25                  30

Gly Asn Val Ala Glu Gly Glu Thr Lys Pro Asp Pro Asp Val Thr Glu
        35                  40                  45

Arg Cys Ser Asp Gly Trp Ser Phe Asp Ala Thr Thr Leu Asp Asp Asn
50                  55                  60

Gly Thr Met Leu Phe Phe Lys Gly Glu Phe Val Trp Lys Ser His Lys
65                  70                  75                  80

Trp Asp Arg Glu Leu Ile Ser Glu Arg Trp Lys Asn Phe Pro Ser Pro
                85                  90                  95

Val Asp Ala Ala Phe Arg Gln Gly His Asn Ser Val Phe Leu Ile Lys
            100                 105                 110

Gly Asp Lys Val Trp Val Tyr Pro Pro Glu Lys Lys Glu Lys Gly Tyr
        115                 120                 125

Pro Lys Leu Leu Gln Asp Glu Phe Pro Gly Ile Pro Ser Pro Leu Asp
    130                 135                 140

Ala Ala Val Glu Cys His Arg Gly Glu Cys Gln Ala Glu Gly Val Leu
145                 150                 155                 160

Phe Phe Gln Gly Asp Arg Glu Trp Phe Trp Asp Leu Ala Thr Gly Thr
                165                 170                 175

Met Lys Glu Arg Ser Trp Pro Ala Val Gly Asn Cys Ser Ser Ala Leu
            180                 185                 190

Arg Trp Leu Gly Arg Tyr Tyr Cys Phe Gln Gly Asn Gln Phe Leu Arg
        195                 200                 205

Phe Asp Pro Val Arg Gly Glu Val Pro Pro Arg Tyr Pro Arg Asp Val
    210                 215                 220

Arg Asp Tyr Phe Met Pro Cys Pro Gly Arg Gly His Gly His Arg Asn
225                 230                 235                 240

Gly Thr Gly His Gly Asn Ser Thr His His Gly Pro Glu Tyr Met Arg
                245                 250                 255

Cys Ser Pro His Leu Val Leu Ser Ala Leu Thr Ser Asp Asn His Gly
            260                 265                 270

Ala Thr Tyr Ala Phe Ser Gly Thr His Tyr Trp Arg Leu Asp Thr Ser
        275                 280                 285

Arg Asp Gly Trp His Ser Trp Pro Ile Ala His Gln Trp Pro Gln Gly
    290                 295                 300

Pro Ser Ala Val Asp Ala Ala Phe Ser Trp Glu Glu Lys Leu Tyr Leu
305                 310                 315                 320

Val Gln Gly Thr Gln Val Tyr Val Phe Leu Thr Lys Gly Gly Tyr Thr
                325                 330                 335

Leu Val Ser Gly Tyr Pro Lys Arg Leu Glu Lys Glu Val Gly Thr Pro
            340                 345                 350

His Gly Ile Ile Leu Asp Ser Val Asp Ala Ala Phe Ile Cys Pro Gly
        355                 360                 365

Ser Ser Arg Leu His Ile Met Ala Gly Arg Arg Leu Trp Trp Leu Asp
    370                 375                 380

Leu Lys Ser Gly Ala Gln Ala Thr Trp Thr Glu Leu Pro Trp Pro His
385                 390                 395                 400

Glu Lys Val Asp Gly Ala Leu Cys Met Glu Lys Ser Leu Gly Pro Asn
                405                 410                 415
```

```
Ser Cys Ser Ala Asn Gly Pro Gly Leu Tyr Leu Ile His Gly Pro Asn
            420                 425                 430

Leu Tyr Cys Tyr Ser Asp Val Glu Lys Leu Asn Ala Ala Lys Ala Leu
            435                 440                 445

Pro Gln Pro Gln Asn Val Thr Ser Leu Leu Gly Cys Thr His
            450                 455                 460

<210> SEQ ID NO 2
<211> LENGTH: 51
<212> TYPE: PRT
<213> ORGANISM: Homo sapiens

<400> SEQUENCE: 2

Cys Ser Asp Gly Trp Ser Phe Asp Ala Thr Thr Leu Asp Asp Asn Gly
1               5                   10                  15

Thr Met Leu Phe Phe Lys Gly Glu Phe Val Trp Lys Ser His Lys Trp
            20                  25                  30

Asp Arg Glu Leu Ile Ser Glu Arg Trp Lys Asn Phe Pro Ser Pro Val
            35                  40                  45

Asp Ala Ala
    50

<210> SEQ ID NO 3
<211> LENGTH: 300
<212> TYPE: PRT
<213> ORGANISM: Homo sapiens

<400> SEQUENCE: 3

Gln Gly Asp Arg Glu Trp Phe Trp Asp Leu Ala Thr Gly Thr Met Lys
1               5                   10                  15

Glu Arg Ser Trp Pro Ala Val Gly Asn Cys Ser Ser Ala Leu Arg Trp
            20                  25                  30

Leu Gly Arg Tyr Tyr Cys Phe Gln Gly Asn Gln Phe Leu Arg Phe Asp
            35                  40                  45

Pro Val Arg Gly Glu Val Pro Pro Arg Tyr Pro Arg Asp Val Arg Asp
    50                  55                  60

Tyr Phe Met Pro Cys Pro Gly Arg Gly His Gly His Arg Asn Gly Thr
65                  70                  75                  80

Gly His Gly Asn Ser Thr His His Gly Pro Glu Tyr Met Arg Cys Ser
            85                  90                  95

Pro His Leu Val Leu Ser Ala Leu Thr Ser Asp Asn His Gly Ala Thr
            100                 105                 110

Tyr Ala Phe Ser Gly Thr His Tyr Trp Arg Leu Asp Thr Ser Arg Asp
            115                 120                 125

Gly Trp His Ser Trp Pro Ile Ala His Gln Trp Pro Gln Gly Pro Ser
            130                 135                 140

Ala Val Asp Ala Ala Phe Ser Trp Glu Glu Lys Leu Tyr Leu Val Gln
145                 150                 155                 160

Gly Thr Gln Val Tyr Val Phe Leu Thr Lys Gly Gly Tyr Thr Leu Val
            165                 170                 175

Ser Gly Tyr Pro Lys Arg Leu Glu Lys Glu Val Gly Thr Pro His Gly
            180                 185                 190

Ile Ile Leu Asp Ser Val Asp Ala Ala Phe Ile Cys Pro Gly Ser Ser
            195                 200                 205

Arg Leu His Ile Met Ala Gly Arg Arg Leu Trp Trp Leu Asp Leu Lys
            210                 215                 220
```

```
Ser Gly Ala Gln Ala Thr Trp Thr Glu Leu Pro Trp Pro His Glu Lys
225                 230                 235                 240

Val Asp Gly Ala Leu Cys Met Glu Lys Ser Leu Gly Pro Asn Ser Cys
                245                 250                 255

Ser Ala Asn Gly Pro Gly Leu Tyr Leu Ile His Gly Pro Asn Leu Tyr
            260                 265                 270

Cys Tyr Ser Asp Val Glu Lys Leu Asn Ala Ala Lys Ala Leu Pro Gln
        275                 280                 285

Pro Gln Asn Val Thr Ser Leu Leu Gly Cys Thr His
    290                 295                 300
```